(12) United States Patent
Dimitsoglou et al.

(10) Patent No.: US 10,111,675 B2
(45) Date of Patent: Oct. 30, 2018

(54) DEVICE FOR FORMING AN OPENING ADAPTED TO RECEIVE A CRANIAL PLUG

(75) Inventors: Aristides Dimitsoglou, Kallithea (GR); Eleftherios Kosmidis, Heraklion Attiki (GR); Dimitrios Karabetsos, Heraklion Creta (GR); Antonios Vakis, Pefki Attikis (GR)

(73) Assignee: N.G. MED SINGLE MEMBER PRIVATE COMPANY, Kifisia Attikis (GR)

( * ) Notice: Subject to any disclaimer, the term of this patent is extended or adjusted under 35 U.S.C. 154(b) by 1725 days.

(21) Appl. No.: 14/412,814

(22) PCT Filed: Mar. 14, 2011

(86) PCT No.: PCT/GR2011/000011
§ 371 (c)(1),
(2), (4) Date: Jan. 5, 2015

(87) PCT Pub. No.: WO2011/110874
PCT Pub. Date: Sep. 15, 2011

(65) Prior Publication Data
US 2015/0164517 A1 Jun. 18, 2015

(30) Foreign Application Priority Data
Mar. 12, 2010 (GR) .............................. 20100100149

(51) Int. Cl.
*A61B 17/16* (2006.01)
*A61B 90/00* (2016.01)

(52) U.S. Cl.
CPC ...... *A61B 17/1659* (2013.01); *A61B 17/1615* (2013.01); *A61B 17/162* (2013.01); *A61B 17/1633* (2013.01); *A61B 2090/034* (2016.02); *A61B 2090/062* (2016.02)

(58) Field of Classification Search
CPC . A61B 17/16; A61B 17/1615; A61B 17/1617; A61B 17/1662; A61B 17/1695
USPC .................................. 606/80, 170, 172, 173
See application file for complete search history.

(56) References Cited

U.S. PATENT DOCUMENTS

| | | | | |
|---|---|---|---|---|
| 3,797,497 A | * | 3/1974 | Crim .................. | A61B 17/1617 606/173 |
| 8,152,809 B1 | * | 4/2012 | Kao .................... | A61B 17/1695 408/202 |

* cited by examiner

*Primary Examiner* — Kathleen Holwerda

(57) ABSTRACT

Device adapted to perform appropriate forming of openings (3) made in the skull (2) during craniotomy with an opening (4) of enlarged diameter that may thereafter be filled with a standardized cranial plug, the device comprising a cylindrical body member (6) with a rear end extending into a shaft (8) coupled in a rotary power supply source and a frontal end provided with a cutting head (8a) with cutting teeth of triangular section and a guide head (10) comprising a first cylindrical portion (10a) having a diameter equivalent to the corresponding diameter of opening (3) that extends forwardly of the cutting head (8a) and is inserted into opening (3) stabilizing the device and allowing subsequent drilling of opening (3) with the cutting head (8a) to form the above-mentioned opening (4) of enlarged diameter, the drilling operation being terminated with the contact of a circumferential ring (7) provided at the frontal end of the cylindrical body member (6) onto the skull (2).

7 Claims, 2 Drawing Sheets

DEVICE FOR FORMING AN OPENING ADAPTED TO RECEIVE A CRANIAL PLUG

THE FIELD OF THE ART

The present invention refers to a device employed in cranial surgery wherein cranial plugs are used to fill the burr holes, i.e. the small openings in the cranium made to facilitate cutting out a skull flap and allow access to a predetermined region of the brain. The device is adapted for appropriately forming a burr hole opened in the skull during craniotomy with a scope of producing a portion of enlarged diameter therein, extending at a depth smaller than the overall depth of the burr hole, thereby allowing employment of a standardised cranial plug of predetermined dimensions to fill such portion of the opening with the enlarged diameter following conclusion of the intended brain surgery and replacement of the skull flap that was removed during the craniotomy.

THE BACKGROUND OF THE INVENTION

A broad variety of surgical tools are known in the prior art particularly employed in performing drilling operations of varying scope and use. Such surgical drilling tools are used in the opening of holes of desired dimensions in the skull with a scope of performing brain surgery, such holes being employed to define the path of craniotomy and removal of a necessary portion of the skull, the so called skull flap that is maintained and is put back in place onto the skull following conclusion of the surgery process. After the post-surgical replacement of the skull flap, the abovementioned holes that had been opened with a scope to effect temporary removal of the skull flap remain uncovered and necessitate coverage.

A variety of tailor made cranial plugs prepared with a raw material of a ductile, rapidly hardening paste has been employed in filling these holes in the skull. However this solution is rather unreliable, has an accuracy inferior to the required standards and may often be rejected by the recipient patient involved.

The object of the present invention is therefore to effectively overcome the disadvantages and drawbacks of the prior art and propose a device that may be employed to appropriately form previously cut openings in the skull so as to render them capable of receiving standardised cranial plugs of predetermined dimensions that will rapidly cover the openings in the most reliable manner, with an optimum accuracy thereby providing a substantially reduced possibility of such cranial plugs being rejected by the recipient patient involved. The required healing period after placement of such cranial plugs is also substantially improved and the aesthetic result obtained is by far the best to be expected.

The device of the invention is adapted to perform appropriate forming of the openings made in the skull during craniotomy with a scope of forming an opening of enlarged diameter within a portion of the previously drilled opening, such opening being thereafter filled with a standardised cranial plug. The device comprises a cylindrical body member with a rear end extending into a shaft being coupled in a rotary power supply source and a frontal end provided with a cutting head with cutting teeth of triangular section. A guide head comprising a first cylindrical portion having a diameter equivalent to the diameter of the previously drilled opening that extends forwardly of the cutting head is inserted into this opening and stabilizes the device, whilst the cutting head advances inwardly therein to form the abovementioned opening of enlarged diameter, wherein the drilling operation is terminated with the contact of a circumferential ring provided at the frontal end of the cylindrical body member of the device onto the skull.

A further object of the invention is to propose an alternative embodiment of the device of the invention capable of being adjusted at a desired selected length of protrusion of the cutting head thereby effecting a differentiated depth of the opening of enlarged diameter that is going to receive the appropriately prepared standardised cranial plug.

These and other objects, characteristics and advantages of the invention will be made apparent in the detailed description of preferred embodiments thereof.

BRIEF DESCRIPTION OF THE DRAWINGS

The invention will be hereinafter described by reference to illustrative embodiments appearing in the appended drawings in which.

DETAILED DESCRIPTION OF PREFERRED EMBODIMENTS

Reference will hereinafter be made to the accompanying drawings for describing illustrative preferred embodiments of the invention.

Figure 1:
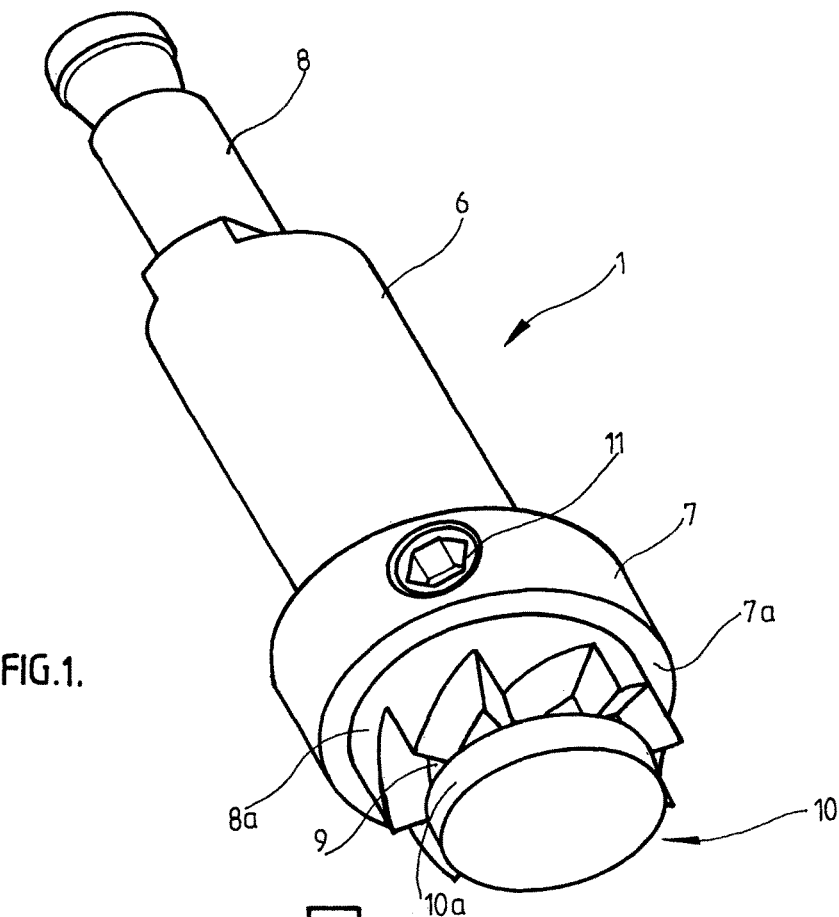
FIG. 1 presents a perspective view of the device of the invention adapted to appropriately forming the openings or burr holes made in the cranium to facilitate cutting out a skull flap during brain surgery with a scope of subsequently filling such openings with cranial plugs.
Figure 3:
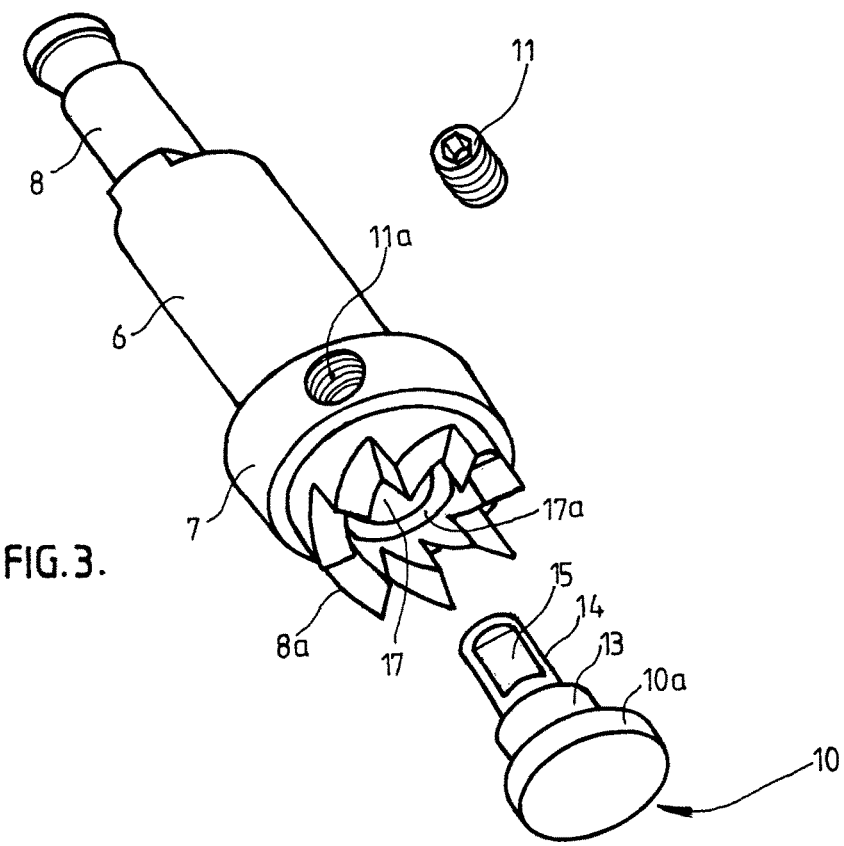
FIG. 3 shows a perspective view of the device of FIG. 1 dismantled in the constituent parts of a main rotary powered surgical drilling instrument, a guide head adapted to defining a predetermined drilling operation and a screw means for fixedly mounting the guide head onto the drilling instrument.
Figures 4A, 4B, 4C:
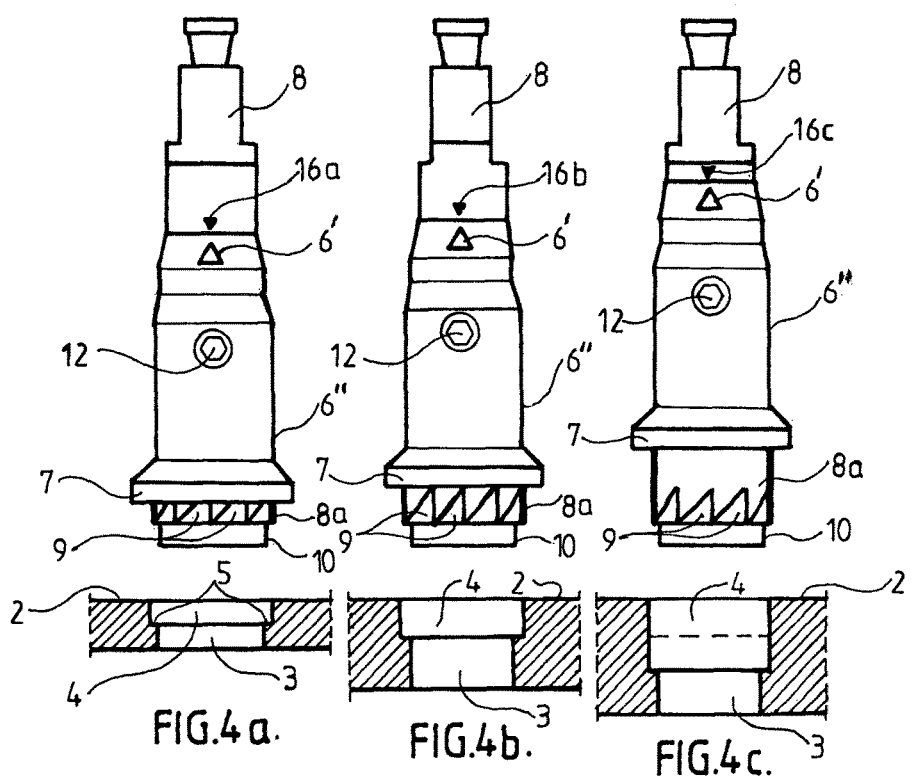
FIGS. 4a-4c show a cross-sectional view of an embodiment of the device of the invention configured so as to perform drilling operations of varying depth into a previously cut opening made in the skull during brain surgery.

According to a preferred, illustrative embodiment of the invention, FIGS. 1 and 3 present a device 1 adapted to perform appropriate forming of the openings or burr holes made in the cranium to facilitate cutting out a skull flap during brain surgery with a scope of subsequently filling such openings with cranial plugs. The device 1 comprises a cylindrical body member 6 with a rear end extending into a shaft 8 having the appropriate configuration for being coupled in a rotary power supply source and a frontal end provided with a cutting head 8a comprising a perimetrical arrangement of cutting teeth, preferably of triangular section. The frontal end of the cylindrical body member 6 comprises a circumferential ring 7 prior to the cutting head 8*a*, such circumferential ring 7 having a diameter larger than the diameter of the cutting head 8*a* and forming a circumferential flat basement 7*a*. A cylindrical opening 17 is provided in the interior of the cutting head 8*a* and a guide head 10 enters and is fixedly mounted within this cylindrical opening 17.

Figure 2A:
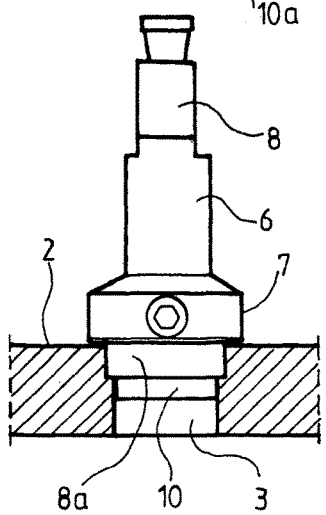
FIG. 2a shows in perspective a detail of a portion of the skull incorporating an opening or burr hole made with a scope of facilitating cutting out a skull flap during brain surgery.
Figure 2B:
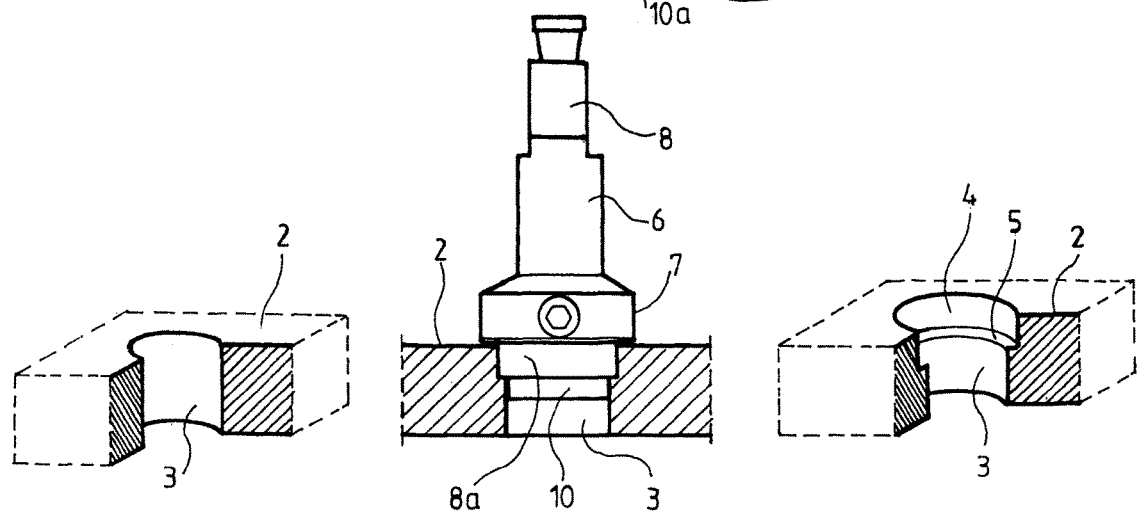
FIG. 2b shows a cross-sectional view of the portion of the skull of FIG. 2a and of the device of the invention having entered into the opening previously made in this portion of the skull with a scope of appropriately forming such opening for the reception of a cranial plug.
Figure 2C:
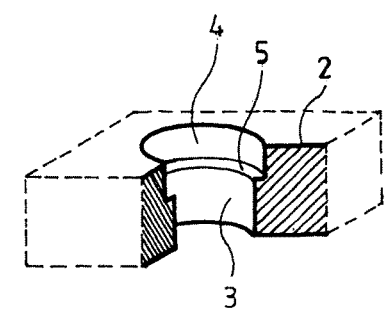
FIG. 2c shows in perspective a detail of a portion of skull of FIG. 2b incorporating an opening or burr hole made with a scope of facilitating cutting out a skull flap during brain surgery following completion of the forming process conducted with the device of the invention, whereby the opening has been adapted for the reception of a cranial plug.

FIGS. 2*a*-2*c* and 4*a*-4*c* depict an illustrative portion of a surface 2 of the skull, wherein a through opening 3 has been drilled with a scope of implementing the craniotomy required in a particular brain surgery operation. The scope of the device of the invention is to appropriately form this opening 3 so as to receive a standardised cranial plug following conclusion of the brain surgery operation and putting back in place the skull flap that had been removed during the craniotomy to allow access in the specified region of the interior of the brain. As shown in FIG. 2*c*, after its appropriate forming implemented with the device of the invention, the through opening 3 comprises a portion 4 extending from the exterior of skull surface 2 up to a desired depth inwardly the same, such portion 4 having a diameter incrementally larger than the diameter of opening 3, so that a flat flange 5 is formed at the borderline of opening 3 with the enlarged opening 4, such flat flange 5 thereafter defining a basement whereupon terminates the insertion of the standardised cranial plug having the diameter of the opening 4 and a length equivalent to the depth of the same, thereby ensuring a precise fit within the opening 4 of the skull with its exterior covering the region of opening 4 and being evenly level with the surrounding exterior surface of the skull.

As illustratively shown in FIG. 3, the aforementioned guide head 10 comprises a first cylindrical portion 10*a* that has a diameter equivalent to the corresponding diameter of the opening 3 so as to firmly fit on the walls of opening 3 when inserted therein, such first cylindrical portion 10*a* extending forwardly of the cutting head 8*a* of the forming device of the invention and having a diameter smaller than the external diameter of the cutting head 8*a* and larger than the internal diameter thereof, wherein the above first cylindrical portion 10*a* concentrically extends into a second cylindrical portion 13 having a diameter smaller than that of the first cylindrical portion 10*a* and equivalent to the interior diameter of the cutting head 8*a* so as to terminate onto a basement flange 17*a* at the frontal end of the device of the invention during the assembly of the guide head 10 within the frontal end of the cylindrical body member 6 of the device of the invention and wherein thereafter the above-mentioned second cylindrical portion 13 of the guide head 10 extends into a cylindrical shaft 14 having a yet smaller diameter than the first cylindrical portion 10*a* and the second cylindrical portion 13 so as to enter within the interior of the cylindrical body member 6 of the device. A portion of the surface of the cylindrical shaft 14 has been removed so as to form flat portions 15. When the guide head 10 is introduced at the frontal end of the cylindrical body member 6 during assembly of the device of the invention, a screw 11 is driven into a threaded side opening 11*a* provided onto the surface of the circumferential ring 7 and screwed therein, so as to be brought in contact with an aforementioned flat portion 15 of the cylindrical shaft 14 and subsequently fixedly mount the guide head 10 onto the frontal end of the cylindrical body member 6 of the device of the invention. Following completion of the assembly process, the aforementioned first cylindrical portion 10*a* of the guide head 10 appropriately covers the central opening 17 of the cutting head 8*a* of the device, the latter being provided with an appropriate arrangement of gaps 9 in between successive cutting teeth thereof, thereby allowing collection of the granulated skull material arising from the forming process conducted by means of the device of the invention within a closed space formed within the interior of the central opening 17 being covered by the first cylindrical portion 10*a* of the guide head 10.

The forming process conducted with the device of the invention comprises a first step of introducing the guide head 10 at the frontal end thereof within a previously cut opening 3 of the skull 2 so that the first cylindrical portion 10*a* thereof firmly fits within the side walls of opening 3 and a second step of initiating drilling into the previously cut opening 3 of the skull 2 and cutting a portion of the side walls of opening 3 with the rotating cutting head 8*a* thereby creating an opening portion 4 that has a diameter larger than the bore of opening 3, such drilling process being terminated when the flat basement 7*a* of the ring 7 of the device comes in contact with the exterior surface of the skull 2.

According to an alternative illustrative embodiment of the invention, the proposed device adapted to form a previously cut opening 3 of the skull so as to allow reception of a cranial plug therein is offered with a capacity of adjustment of the depth of intrusion thereof into a previously cut opening 3 of the skull thereby leading to usage of cranial plugs of accordingly varying length. In this case the device 1 comprises the same guide head 10 and a pair of collaborating parts replacing the previously single cylindrical body member 6 that had a rear end extending into a shaft 8 having the appropriate configuration for being coupled in a rotary power supply source and a frontal end provided with a cutting head 8*a* comprising a perimetrical arrangement of cutting teeth. According to this alternative, illustrative embodiment, the device comprises an internal shaft 8-8*a* with the rear end 8 appropriately configured for being connected to a rotary power supply source and the frontal end provided with the cutting head 8*a*, and on the other hand, a mobile external cylindrical body member 6" provided with the circumferential ring 7 that has a diameter larger than the diameter of the cutting head 8*a* and forms the circumferential flat basement 7*a* that determines the end of intrusion of the device 1 within an opening 3 in the skull, wherein this mobile external cylindrical body member 6" is adapted to slide along the internal shaft 8-8*a* and is provided with a pointer 6', such pointer being alternatively brought in a desired position of an array of alternative positions marked onto the circumference of shaft 8-8*a* so as to define a varying depth of intrusion of the device within a previously drilled opening 3 in the skull with a scope of appropriately forming the same for the reception of cranial plugs that have correspondingly varying lengths so as to fit within the above-mentioned varying depths of intrusion of the device within the previously drilled opening 3 in the skull. By way of example, an arrangement of three consecutive parallel marking lines 16*a*, 16*b*, 16*c* is provided at the circumference of shaft 8-8*a* and pointer 6' of the external sliding cylindrical body member 6" is alternatively brought into alignment with any of these three positions 16*a*, 16*b*, 16*c* thereby defining the correspondingly increasing depth of intrusion of the device within an opening 3 of the skull as consecutively depicted in FIGS. 4*a*, 4*b* and 4*c*. In the case of this alternative embodiment of the device of the invention a side opening is provided at the circumference of the mobile external cylindrical body member 6", wherein is being driven a headless screw 12 that fixedly connects the external cylindrical body member 6" onto the interior shaft 8-8*a*.

It is hereby noted that any changes or amendments in the above that do not constitute a new inventive step are considered part of the scope and aims of the present invention as defined in the appended claims.

The invention claimed is:

1. A device adapted to perform appropriate forming of openings (3) made in a skull (2) to facilitate cutting out a skull flap during brain surgery with a scope of subsequently filling such openings with standardised cranial plugs, said device characterised in that it comprises:

a cylindrical body member (6) with a rear end extending into a shaft (8) having an appropriate configuration for being coupled in a rotary power supply source and a frontal end provided with a cutting head (8a) comprising a perimetrical arrangement of cutting teeth of triangular section, said frontal end of the cylindrical body member (6) comprising a circumferential ring (7) rearward of the cutting head (8a), said circumferential ring (7) having a diameter larger than an external diameter of the cutting head (8a) and forming a circumferential flat basement (7a), and a guide head (10) comprising a first cylindrical portion (10a) that has a diameter, smaller than the external diameter of the cutting head (8a) and larger than an internal diameter thereof, equivalent to the corresponding diameter of an opening (3) made in the skull (2) so as to firmly fit onto side walls of said opening (3) when inserted therein, said first cylindrical portion (10a) extending forwardly of said cutting head (8a), a second cylindrical portion (13) extending rearwardly said first cylindrical portion (10a), said second cylindrical portion (13) having a diameter smaller than the diameter of the first cylindrical portion (10a) and equivalent to the internal diameter of the cutting head (8a) so as to terminate onto a basement flange (17a) provided at the frontal end of said cylindrical body member (6), said second cylindrical portion (13) extending into a shaft (14) having a yet smaller diameter than said first cylindrical portion (10a) and said second cylindrical portion (13), said shaft (14) entering through an opening (17) in an interior of the cylindrical body member (6) of the device, said guide head (10) being fixedly mounted onto said cylindrical body member (6) with said first cylindrical portion (10a) thereof extending forwardly said cutting head (8a), whereby a previously cut opening (3) of the skull (2) is appropriately formed for the reception of a cranial plug through introduction of said first cylindrical portion (10a) of the guide head (10) at an inlet of said previously cut opening (3) and firm fitting thereof within the side walls of said previously cut opening (3) and subsequent initiating rotation of said cutting head (8a) drilling into the previously cut opening (3) and cutting a portion of the side walls thereof thereby creating an enlarged opening (4) appropriately formed for the reception of said cranial plug, said enlarged opening (4) having a diameter larger than a diameter of the previously cut opening (3) and extending at a depth corresponding to the length of the cutting head (8a) protruding forwardly said circumferential ring (7), wherein operation of said cutting head (8a) is terminated when said flat basement (7a) of said circumferential ring (7) comes in contact with an exterior surface of the skull (2).

2. The device adapted to perform appropriate forming of openings (3) made in the skull (2) as claimed in claim 1, characterised in that a flat flange (5) is formed at a borderline of the previously cut opening (3) with the enlarged opening (4), said flat flange (5) thereafter defining a basement that terminates the insertion of a selected standardised cranial plug having the diameter of said enlarged opening (4) and a length equivalent to the depth of the same, whereby a precise fit of said selected standardised cranial plug within the enlarged opening (4) of the skull (2) is obtained with one end of the cranial plug sitting onto said flat flange (5) within said previously cut opening (3) and the other end thereof adapted to be evenly level with the surrounding exterior surface of the skull (2).

3. The device adapted to perform appropriate forming of openings (3) made in the skull (2) as claimed in claim 1, characterised in that flat portions (15) are formed around a surface of said shaft (14) of said guide head (10) through removal of parts of the surface thereof and in that said circumferential ring (7) is provided with a threaded side opening (11a), wherein said guide head (10), being introduced through said opening (17) at the frontal end of said cylindrical body member (6) during assembly of the device, is fixedly mounted thereupon by means of a screw (11) driven into said threaded side opening (11a) and screwed therein so as to be brought in contact with one of said flat portions (15) of said shaft (14) of said guide head (10).

4. The device adapted to perform appropriate forming of openings (3) made in the skull (2) as claimed in claim 1, characterised in said cutting head (8a) being provided with an arrangement of gaps (9) in between successive cutting teeth thereof, said gaps (9) allowing collection of granulated skull material arising from the forming of openings within a closed space formed within the opening (17) of the interior of the cylindrical body member (6) being covered by said first cylindrical portion (10a) of the guide head (10).

5. The device adapted to perform appropriate forming of openings (3) made in the skull (2) as claimed in claim 1, characterised in that a capacity of adjustment of the depth of intrusion of said cutting head (8a) into a previously cut opening (3) of the skull is obtained that leads to usage of cranial plugs of accordingly varying length, with said cylindrical body member (6) further comprising a mobile external cylindrical body member (6") provided with said circumferential ring (7) that has a diameter larger than the diameter of the cutting head (8a) and forms the circumferential flat basement (7a) that determines the end of intrusion of the device within an opening (3) in the skull, said mobile external cylindrical body member (6") being adapted to slide along said shaft (8) and be fixedly mounted at a desired position thereupon that defines a varied length of protrusion of said cutting head (8a) and accordingly a varied depth of intrusion thereof into said opening (3) in the skull that produces an accordingly varied depth of said enlarged opening (4) with said flat flange (5) whereupon sits a cranial plug of accordingly varied length.

6. The device adapted to perform appropriate forming of openings (3) made in the skull (2) as claimed in claim 5, characterised in that said mobile external cylindrical body member (6") is provided with a pointer (6') and the shaft (8) is provided with an arrangement of three consecutive parallel marking lines (16a, 16b, 16c) at the circumference thereof, said pointer (6') being alternatively brought into alignment with any of three positions determined by means of said three consecutive parallel marking lines (16a, 16b, 16c) thereby defining a correspondingly varying length of protrusion of said cutting head (8a) forwardly said circumferential ring (7) and a correspondingly varying depth of intrusion of the device within an opening (3) of the skull (2), said varying depth of intrusion of the device within said opening (3) of the skull (2) producing a correspondingly varying depth of said enlarged opening (4) that is thereafter being filled with a cranial plug of correspondingly varying length.

7. The device adapted to perform appropriate forming of openings (3) made in the skull (2) as claimed in claim 6, characterised in that a headless screw (12) is employed and is being driven into a side opening provided at the circumference of said mobile external cylindrical body member (6") with a scope of fixedly connecting said external cylindrical body member (6") onto said shaft (8) after having brought said pointer (6') of said mobile external cylindrical body member (6") into alignment with a selected marking line of said three consecutive parallel marking lines (16*a*, 16*b*, 16*c*) provided onto said shaft (8).

* * * * *